United States Patent [19]

Bayssat et al.

[11] Patent Number: 4,512,994
[45] Date of Patent: Apr. 23, 1985

[54] LONG-ACTING THEOPHYLLINE IN MEDICINAL FORM

[75] Inventors: Michel Bayssat, Charbonnieres; Maryse Belleville; Marcel Grand, both of Lyons, all of France

[73] Assignee: Lipha, Lyonnaise Industrielle Pharmaceutique, Lyons, France

[21] Appl. No.: 491,025

[22] Filed: May 3, 1983

[30] Foreign Application Priority Data

May 4, 1982 [FR] France .................. 82 07695
Apr. 14, 1983 [FR] France .................. 83 06075

[51] Int. Cl.³ .................................. A61K 31/52
[52] U.S. Cl. .................................. 514/374; 514/617; 514/621
[58] Field of Search .................. 424/253

[56] References Cited

U.S. PATENT DOCUMENTS 3,780,102 12/1973 Bayssat et al. .................. 424/300

FOREIGN PATENT DOCUMENTS 2040181 1/1971 France .................. 424/300

OTHER PUBLICATIONS

Cutting's Handbook of Pharmacology, 4th Ed., 1967, pp. 294-296.
Chemical Abstracts vol. 92, Jun. 23, 1980, No. 25 (92: 208747f Inhibition by Idrocilamide of the Disposition of Caffeine)(J. L. Brazier) 1-Pharmacodynamics.
European Journal of Medicinal Chemistry (Chimica Therapeutica) vol. IX, Sep.-Oct. 1974, No. 5.

Primary Examiner—Leonard Schenkman
Attorney, Agent, or Firm—Browdy and Neimark

[57] ABSTRACT

Long-acting forms of theophylline for use in treating asthma comprise theophylline associated with a compound of the substituted cinnamamide type of the general formula

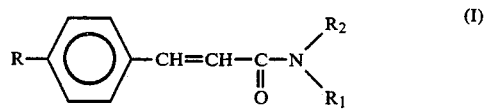

wherein R is hydrogen, a hologen or an acetyl radical; $R_1$ is hydrogen or the methyl radical; $R_2$ is

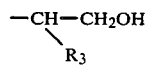

wherein $R_3$ is hydrogen or the methyl radical; or $R_1$ and $R_2$ together with the adjacent nitrogen tom form the 2,2-dimethyl-3-oxazolidinyl group.

13 Claims, 2 Drawing Figures

LONG-ACTING THEOPHYLLINE IN MEDICINAL FORM

FIELD OF INVENTION

This invention relates to a medicinal form of long-acting theophylline.

BACKGROUND

Theophylline, also known as 1,3-dimethylxanthine, is a bitter tasting white powder, slightly soluble in water, of the formula

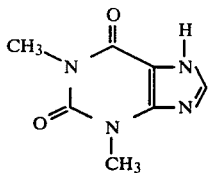

It has a bronchodilating action due to a relaxation of the bronchial smooth muscles; it is active toward all bronchoconstrictive agents. It also has an inhibiting action on mastocytes by partially inhibiting their degranulation with the release of histamine in hypersensitivity reactions.

As R. W. Butcher and E. W. Sutherland, J. Biol. Chem., vol. 237, pp 1244–1250 (1962) showed, this activity seems linked to a competitive inhibition on the phosphodiesterase, an enzyme that catalyzes the transformation of cyclic AMP (cyclic adenosine 3',5'-monophosphate) into 5'-AMP. It results in a tissue increase of cyclic AMP which would be responsible for the activity of the theophylline.

Theophylline has been used for a long time in treating asthma, but its early use had suffered some discredit, the product being considered poorly tolerated and ineffective. New determination techniques by high-performance liquid chromatography and by immunoenzymological methods now permit a simple and exact determination of theophylline blood levels. These methods have brought about progress in the use of the medicine and theophylline is now beginning to take an important place in treating asthma. Although the use of adrenocorticosteroids may be necessary at times in treating the asthma, bronchodilating medicines hold a dominant place in the therapy and theophylline is undoubtedly the most useful of these bronchodilating medicines.

Theophylline is absorbed very well orally. On the other hand, rectal absorption is very irregular. Intrapulmonary administration by aerosol is ineffective.

An effect-blood concentration relation has been established. For a blood level between 5 and 20 mg/l, improvement of the pulmonary vital capacity is proportional to the logarithm of the concentration. Above a 20 mg/l concentration, intolerance signs can appear: digestive disorders, nervous troubles, cardiac troubles, then neurological symptoms.

Most of the theophylline is metabolized at the hepatic level to give inactive metabolites eliminated by the kidneys. The half-life can vary with age and the individuals; on the average, it is close to 6 hours in a normal adult, but half-lives of 4 hours are not uncommon.

For good results, the patients must absorb a dose of medicine every 6 hours. However, since asthma takes on a chronic nature, it is hardly possible to achieve carefully followed treatment with such frequent doses regularly space over the day.

Accordingly, various galenical formulas have been proposed, for example of the microgranule type, from which theophylline is slowly released in the digestive tract.

However, it is desirable to obtain more lasting blood levels, which would make it possible to simplify the dosage, by reducing the number of doses of medicine taken and also by reducing the fluctuations of the blood level.

SUMMARY

Accordingly, an association was sought of theophylline with a product for maintaining the theophylline blood level within favorable therapeutic limits with long period of action. Such a theophylline association has now been found that remedies the drawback of the relatively short half-life of the theophylline and makes it possible, after a dose, to obtain a theophylline blood level that is stable and long with a therapeutic effectiveness of 24 hours a day.

According to the invention, theophylline or a derivative thereof is associated with a compound of the substituted cinnamide type of the formula

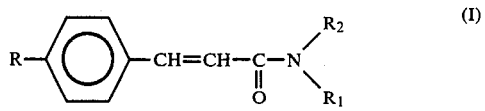

wherein R is hydrogen, a halogen or the acetyl radical; $R_1$ is hydrogen or the methyl group; $R_2$ is a group of the formula

wherein $R_3$ is hydrogen or methyl; or $R_1$ and $R_2$ can also form, with the adjacent nitrogen atom, the 2,2-dimethyl-3-oxazolidinyl group of the formula:

DETAILED DESCRIPTION OF EMBODIMENTS

Figure 1:
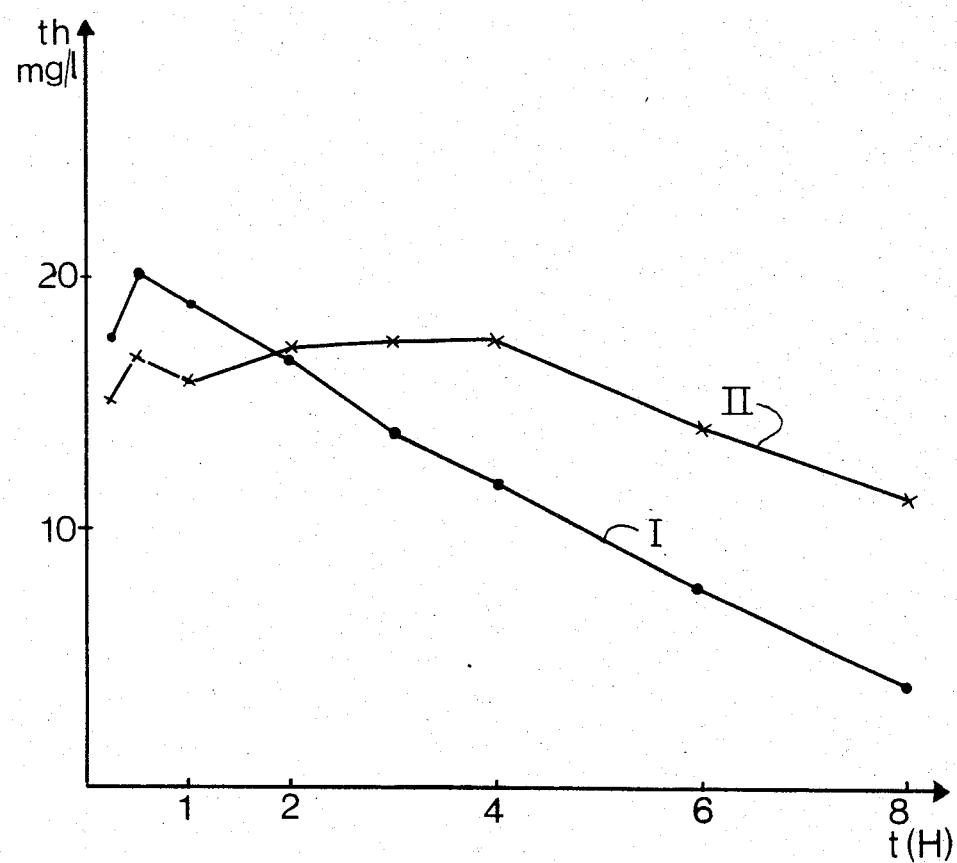
FIG. 1 is a concentration/time graph showing advantages of the invention.

Of the compounds of the substituted cinnamamide family that can be associated with theophylline there can be cited particularly the derivatives N-(2-hydroxyethyl)cinnamamide; N-(2-hydroxyethyl)-4-chlorocinnamamide; N-methyl, N-(2-hydroxyethyl)cinnamamide; N-[2-(1-hydroxypropyl)]cinnamamide; N-(2-hydroxyethyl)-4-fluorocinnamamide; N-(2-hydroxyethyl)-4-acetylcinnamamide; 3-(4-chlorocinnamoyl)2,2-dimethyloxazolidine; 2,2-dimethyl-3-(4-fluorocinnamoyl)oxazolidine and 3-cinnamoyl-2,2-dimethyloxazolidine.

The derivative for which $R_2$ is the group represented by formula II are obtained by the methods described in the LIPHA French Pat. No. 2,040,181. For example, a cinnamoyl chloride of formula

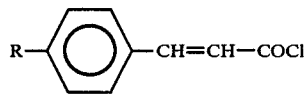

(IV)

can be advantageously be condensed with an amine of the general formula

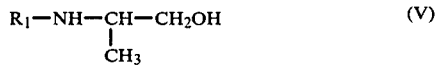

(V)

wherein R, $R_1$ and $R_3$ have the same meaning as above. The reaction is performed in an inert solvent such as dioxane, tetrahydrofuran or chloroform, in the presence of an alkaline agent which can be an alkaline carbonate or bicarbonate, an organic base such as pyridine or triethylamine or in an excess of the amine of formula V. The reaction is performed at temperatures between 0° C. and the boiling point of the solvent used.

Examples of such compounds are as follows:

Compound I: N-(2-hydroxyethyl)cinnamamide, $C_{11}H_{13}NO_2$, M=191.22, crystallized in the form of beautiful white crystals, melting point=100.5°-102.5° C., has a toxicity of $LD_{50}$ orally in mice, of 3,000 mg/kg (common name idrocilamide).

Compound II: N-(2-hydroxyethyl)-4-chlorocinnamamide, $C_{11}H_{12}ClNO_2$, M=225.68, crystallizes in the form of white needles, melting point=137°-138.5° C., $LD_{50}$ orally in mice 1,600 mg/kg.

Compound III: N-methyl, N-(2-hydroxyethyl)cinnamamide, $C_{12}H_{15}NO_2$, M=205.25, crystallizes in the form of a white powder, melting point=79°-81° C., oral $LD_{50}$ in mice 3,000 mg/kg.

Compound IV: N-[2-(1-hydroxypropyl)]cinnamamide, $C_{12}H_{15}NO_2$, M=205.25, small white flakes, melting point=144°-146° C., oral $LD_{50}$ in mice 3,200 mg/kg.

Compound V: N-(2-hydroxyethyl)-4-fluorocinnamamide, $C_{11}H_{12}FNO_2$, M=209.22, melting point=100°-102° C., oral $LD_{50}$ in mice greater than 3,200 mg/kg.

Compound VI: N-(2-hydroxyethyl)-4-acetylcinnamamide, $C_{13}H_{15}NO_3$, M=233.26, melting point=124°-125° C., oral $LD_{50}$ in mice 3,200 mg/kg.

Compounds V and VI are new chemical products not described in French Pat. No. 2,040,181.

The derivatives for which $-NR_1R_2$ represent the 2,2-dimethyl-3-oxazolidinyl group can be prepared by condensing ethanolamine on acetone in a first stage to provide an intermediate oxazolidine which does not have to be isolated, then reacting a cinnamoyl chloride of formula IV on such oxazolidine. The reaction is advantageously performed with an excess of ethanolamine. Examples of compounds so produced are:

Compound VII: 3-(4-chlorocinnamoyl)-2,2-dimethyloxazolidine, $C_{14}H_{16}ClNO_2$, M=265.73, white crystals, melts at 107.5°-109.5° C., oral $LD_{50}$ in mice greater than 3,200 mg/kg.

Compound VIII: 2,2-dimethyl-3-(4-fluorocinnamoyl)oxazolidine, $C_{14}H_{16}FNO_2$, M=249.27, melting point=106°-108° C., oral $LD_{50}$ in mice 2,000 mg/kg.

Compound IX: 3-cinnamoyl-2,2-dimethyloxazolidine, $C_{14}H_{17}NO_2$, M=231.29, melting point=107°-109° C., oral $LD_{50}$ in mice greater than 3,200 mg/kg.

Examples of preparation of the new chemical products are given by way of nonlimiting example.

EXAMPLE 1

3-(4-chlorocinnamoyl)-2,2-dimethyloxazolidine

There were added, drop by drop, 13.4 g (0.22 mole) of ethanolamine to 30 cc of acetone. The mixture was heated. When it returned to room temperature, a solution of 18.3 g (0.09 mole) of 4-chlorocinnamoyl chloride in 20 cc of acetone were added, while the temperature was kept between 15° and 20° C., then stirred for 2 hours at room temperature. The reaction medium was diluted with water. The 3-(4-chlorocinnamoyl)-2,2-dimethyloxazolidine was separated in the form of white crystals. It was filtered, washed with water, dried and recrystallized in heptane. Melting point=107.5°-109.5° C.

| Percentage analysis $C_{14}H_{16}ClNO_2$ M = 265.73 | | | | |
|---|---|---|---|---|
| | C % | H % | Cl % | N % |
| Calculated | 63.29 | 6.07 | 13.35 | 5.27 |
| Found | 63.16 | 6.20 | 13.40 | 5.28 |

IR (KBr) $\nu$ (C=O)=1,660 cm$^{-1}$.

RMN (CDCl$_3$) $\delta$=1.7 ppm (singlet, 4H) 3.6-4.3 (multiplet, 4H) 6.6 (doublet, J=14 Hz, 1H) 7.2-7.6 (complex mass, 4H) 7.6 (doublet, J=14 Hz, 1H).

EXAMPLE 2

N-(2-hydroxyethyl)-4-fluorocinnamamide

A solution of 374 g (2.03 moles) of 4-fluorocinnamoyl chloride in 2 l of dioxane was added, drop by drop at 20° C., to a solution of 297 g (4.87 moles) of ethanolamine in 2 l of dioxane. The reaction medium was stirred for 3 hours at room temperature, left overnight and concentrated under low pressure. The residue was taken up by a sodium bicarbonate solution. The precipitate of N-(2-hydroxyethyl)-4-fluorocinnamamide was filtered, washed with water and dried. Yield 351 g (or 83% of theory). The product was purified by recrystallization in ethylacetate. Melting point=100°-102° C.

| Percentage analysis $C_{11}H_{12}FNO_2$ M = 209.22 | | | | |
|---|---|---|---|---|
| | C % | H % | F % | N % |
| Calculated | 63.14 | 5.78 | 9.08 | 6.70 |
| Found | 6309 | 5.68 | 9.32 | 6.72 |

IR (KBr): $\nu$ (C=O)=1,660 cm$^{-1}$.

EXAMPLE 3

N-(2-hydroxyethyl)-4-acetylcinnamamide

A mixture of 9.5 g (0.05 mole) of 4-acetylcinnamic acid [obtained according to G. H. Cleland, J. Org. Chem., 34, 744 (1969)], of 30 g of thionyl chloride and 40 cc of benzene was brought to reflux for 20 minutes. The solution was concentrated dry under low pressure. The residual solid was dissolved in 100 cc of dioxane and the resulting solution was added, dropy by drop at a temperature of 20° C., to a solution of 9.3 g (0.15 mole) of ethanolamine in 50 cc of dioxane. The mixture was stirred for 1 hour at room temperature, poured into a mixture of 500 g of ice and 20 cc of 10N hydrochloric acid then extracted with chloroform. The organic phase was washed with water and dried on sodium sulfate. By evaporation of the solvent under low pressure there was obtained N-(2-hydroxyethyl)-4-acetylcinnamamide which was purified by recrystallization in ethylacetate. Melting point=124°–125° C. Yield: 4.2 g (36% of theory).

| Percentage analysis $C_{13}H_{15}NO_3$ M = 233.26 | | | |
|---|---|---|---|
| | C % | H % | N % |
| Calculated | 66.93 | 6.48 | 6.01 |
| Found | 66.80 | 6.35 | 612 |

IR (KBr) $\nu$ (C=O)=1,680 and 1,660 cm$^{-1}$.

EXAMPLE 4

2,2-dimethyl-3-(4-fluorocinnamoyl)oxazolidine

Operating as in example 1 starting with 4-fluorocinnamoyl chloride, there was obtained 3-(4-fluorocinnamoyl)-2,2-dimethyloxazolidine. Yield: 77%; melting point=106°–108° C. (hexane-ethylacetate).

| Percentage analysis $C_{14}H_{16}FNO_2$ M = 249.27 | | | | |
|---|---|---|---|---|
| | C % | H % | F % | N % |
| Calculated | 67.45 | 6.47 | 7.62 | 5.62 |
| Found | 67.43 | 6.65 | 7.71 | 5.73 |

EXAMPLE 5

3-cinnamoyl-2,2-dimethyloxazolidine Compound VIII

Operating as in example 1 starting with cinnamoyl chloride, there was obtained 3-cinnamoyl-2,2-dimethyloxazolidine. Yield: 74%. Melting point 107°–109° C. (hexane-ethylacetate).

| Percentage analysis $C_{14}H_{17}NO_2$ M = 231.29 | | | |
|---|---|---|---|
| | C % | H % | N % |
| Calculated | 72.69 | 7.41 | 6.06 |
| Found | 72.62 | 7.42 | 6.05 |

An animal model was found and developed making it possible to show the extended action of theophylline associated with N-(2-hydroxyethyl)cinnamamide (Compound I). Wistar breed male rats, weight 220–240 g, after fasting for 16 hours, received an oral dose of theophylline in solution in a water.

Half of the animals received idrocilamide (Compound I) in suspension in 5% gum arabic at the same time as the theophylline, the other half receiving only gum arabic. The theophylline was administered at a dosage of 15 mg/kg, and the idrocilamide at a dosage of 100 mg/kg. Groups of the so-treated animals were killed by carotid section 15', 30', 1 h, 2 h, 3 h, 4 h, 6 h, and 8 h after administration of the theophylline. The blood was collected in herparinized, centrifuged tubes, and the plasma was decanted. The theophylline blood level was determined in plasma samples after extraction by liquid chromatography.

The averages of the theophylline blood levels obtained and the pharmacokinetic parameters calculated are given in Table 1 below.

TABLE 1

| Concentration in mg/l theophylline after | Animals receiving only theophylline. Average (standard deviation) | | Animals receiving theophylline = idrocilamide. Average deviation) | | |
|---|---|---|---|---|---|
| 15 min. | 17.54 | (5.77) | 14.94 | (3.19) | NS |
| 30 min. | 20.26 | (4.88) | 16.68 | (2.29) | NS |
| 1 Hour | 18.86 | (3.09) | 15.79 | (1.39) | NS |
| 2 Hours | 16.69 | (1.95) | 17.26 | (3.46) | NS |
| 3 Hours | 13.93 | (2.05) | 17.57 | (2.21) | S |
| 4 Hours | 11.96 | (2.43) | 17.74 | (1.53) | S |
| 6 Hours | 8.04 | (2.17) | 14.10 | (2.81) | S |
| 8 Hours | 4.32 | (1.91) | 11.51 | (3.26) | S |
| aged→8 Hours | | | | | |
| mg/l- 1 Hour | 95.10 | | 123 | | |
| Plasma half-life in hours | 3.47 | | 6.42 | | |
| area→∞ | | | | | |
| mg/l-1 Hour | 116.70 | | 229.60 | | |

NS = not significant,
S = significant

This table shows the following findings:

(1) The maximum blood concentration of theophylline was not increased: 20.26 for theophylline alone, 17.74 for its association with idrocilamide;

(2) The blood concentrations of theophylline obtained in association with idrocilamide were significantly greater than those obtained with theophylline alone, starting 3 hours after the administration and continuing to the end of the test. At 8 hours, the concentration was 2.7 times higher;

(3) The half-life calculated from the maximum increased 85% by simultaneous administration of idrocilamide;

(4) The area under the curve of concentrations as a function of time was increased 29.4% up to 8 hours and 166% if extrapolated to infinity.

FIG. 1 of the accompanying drawing shows the theophylline concentration curves as a function of time after a dose of theophylline alone or with idrocilamide; from these curves it is possible to see the stability of theophylinemia after association with idrocilamide and the considerable increase of bioavailability. The time in hours is plotted on the x-axis, t(H) and the concentration in mg/l of theophylline Th mg/l on the y-axis. Curve I corresponds to theophylline alone and curve II to the association of theophylline+idocilamide.

This model made it possible to see that a certain number of structural analogs of N-(2-hydroxyethyl)cinnamamide have, in animals, the same properties of providing a considerable increase in the area under the theophylline curve as a function of time (as shown in FIG. 1, for example) when they are administered as associates with theophylline. Various compounds of the invention gave, in the test described above, the results set forth in Table 2 below.

The cinnamamides tested, the results of which are reported in Table 2 below, were tested as described above with regard to Table 1, the theophylline being administered at 15 mg/kg and the cinnamamide at 100 mg/kg.

TABLE 2

|  | Maximum concentration mg/l | Concentration at 8 Hours mg/l | Plasma half-life hour | Area→ ∞ mg/l - 1 Hour |
|---|---|---|---|---|
| Compound I | 17.74 | 11.51 | 6.42 | 229.60 |
| Compound II | 16.80 | 12.75 | 10 | 306.70 |
| Compound III | 20.50 | 7.58 | 4.50 | 160 |
| Compound IV | 19.70 | 11.86 | 9.20 | 286 |
| Compound V | 22.30 | 15.46 | 16.10 | 501.70 |
| Compound VI | 18 | 10.27 | 10 | 269.40 |
| Compound VII | 21.30 | 14.81 | 11.40 | 385.60 |
| Compound VIII | 21.17 | 11.93 | 8.5 | 294 |
| Compound IX | 22.5 | 13.36 | 7.3 | 288.7 |

The association of theophylline and a substituted cinnamamide compound according to the invention constitutes a medicine that can be used in the applications of theophylline and its derivatives in treating asthma.

Associations of theophylline with a cinnamamide compound substituted by the dimethyloxazolidinyl group proves to be very advantageous, particularly that with 3-(4-chlorocinnamoyl)-2,2-dimethyloxazolidine and 3-cinnamoyl-2,2-dimethyloxazolidine.

The optimum proportions of the substituted cinnamamide derivative in the association depend on the age and weight of the patients. The cinnamamide derivative has an effect at the theophylline metabolizing level, even in a slight dose. It can be associated with theophylline in a theophylline: cinnamamide ratio of about 1:0.1–7 (molar), preferably 2:1 to 1:4 (by weight) depending on the patient and the galenical form.

Theophylline can be introduced in the association in free form or derivative form, i.e. combined, for example, with ethylenediamine (euphylline, aminophylline). In addition, the use of theophylline and aminophylline together can be administered.

The unit amount in association of theophylline active principle or its derivative+substituted cinnamamide can vary between 50 and 1200 mg. A treatment of two doses per day every 12 hours is desirable.

Some formulations associating theophylline or aminophylline with a substituted cinnamamide compound according to the invention, which can be used in therapy, are given below by way of illustration. The proportions of the cinnamamide derivative in the association can vary to take into account particularly the age and weight of the patients.

No. 1—Tablets

| Theophylline | 200 mg |
|---|---|
| Substituted cinnamamide | 200 mg |
| Lactose | 34 mg |
| Starch | 33 mg |
| Gelatin | 10 mg |
| Alginic acid | 20 mg |
| Magnesium stearate | 3 mg |
| | 500 mg |

No. 2—Tablets that can be cut into small rods

| Theophylline | 200 mg |
|---|---|
| Substituted cinnamamide | 400 mg |
| Lactose | 50 mg |
| Starch | 50 mg |
| Gelatin | 15 mg |
| Alginic acid | 30 mg |
| Magnesium stearate | 5 mg |
| | 750 mg |

No. 3—Sugar-coated tablets

| | A | B |
|---|---|---|
| Theophylline | 200 mg | 100 mg |
| Substituted cinnamamide | 100 mg | 100 mg |
| Lactose | 37 mg | 40 mg |
| Starch | 36 mg | 40 mg |
| Gelatin | 8 mg | 6 mg |
| Alginic acid | 16 mg | 12 mg |
| Magnesium stearate | 3 mg | 2 mg |
| | 400 mg | 300 mg |
| Sugar-coating, sufficient amount | 600 mg | 500 mg |

Sugar-coating: sugar, gum arabic, gelatin, talc, white wax.

No. 4—Gastroresistant tablets

Preparation of tablets as in formula 3. Before sugar-coating, the tablets are made gastroresistant by application of hydroxypropylmethylcellulose phthalate in solution in acetone-isopropanol.

No. 5—Suppositories

Aminophylline: 300 mg
Substituted cinnamamide: 100 mg
Semisynthetic glycerides sufficient for 1 suppository, about 3 g.

No. 6—Injectable solution

| | A | B |
|---|---|---|
| Theophylline | 100 mg | 50 mg |
| Substituted cinnamamide | 15 mg | 15 mg |
| Sodium anisate | 300 mg | 150 mg |
| Ethanol at 96° | 0.25 ml | 0.25 ml |
| Water ppi sufficient for | 5 ml | 5 ml |

CLINICAL EXAMPLE I

A series of comparative clinical tests were conducted. Five male adults asthma patients took a simultaneous dose of 200 mg theophylline and 100 mg idocrilamide twice a day orally, at 0800 and 2000 hours. On the 4th day, after establishment of a state of equilibrium, the theophylline blood level in the patients under treatment was determined at various times. The determinations were made by highpressure liquid chromatography (Waters apparatus, Lichrosorb RP 18 adsorbent of Merck, methanol, formamide, monopotassium phosphate solvent. Detection by UV spectrophotometry). The averages of the values obtained appear in Table 3 below.

TABLE 3

| Time | Blood concentration in theophylline |
|---|---|
| before morning dose, 4th day | 9.5 mg/l |
| 2 hours after morning dose | 11.5 mg/l |
| 4 hours after | 12 mg/l |
| 8 hours after | 11.5 mg/l |
| 12 hours after | 10 mg/l |

The following observations can be made:

(1) In the morning, before the medicine was taken, the theophylline blood level was 9.5 mg/l, i.e., in an active concentration zone. Since the lowest concentration was involved, since it was farthest from taking the medicine, this means that during the night the blood concentration was sufficient to assure therapeutic activity.

(2) During this 4th day, after the morning dose, the blood level underwent a moderate increase, overall remaining in a zone between 10 and 15 mg/l. The blood level is therefore stable.

(3) Twelve hours after the morning dose and before the evening dose, the blood level was still 10 mg/l, a sufficient level to assure therapeutic action.

It can therefore be concluded that with this theophylline + idrocilamide association, there is obtained a stable and extended level of theophylline providing a therapeutic effectiveness 24 hours a day.

CLINICAL EXAMPLE II (COMPARATIVE)

The above results are to be compared with those obtained under the same conditions, with administration of 200 mg of theophylline only; they are given in Table 4 below.

TABLE 4

| Time | Blood concentration in theophylline |
|---|---|
| before morning dose, 4th day | 2 mg/l |
| 2 hours after morning dose | 7.5 mg/l |
| 4 hours after | 10.5 mg/l |
| 8 hours after | 5.5 mg/l |
| 12 hours after | 1.5 mg/l |

Figure 2:
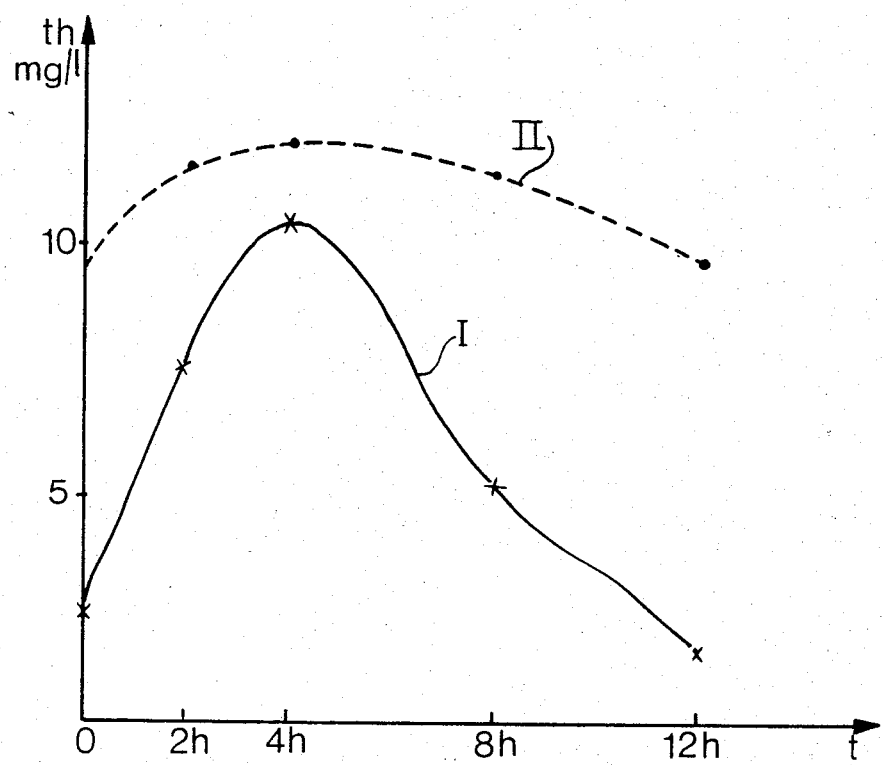
FIG. 2 is a graph showing clinical results according to the invention.

The graph in FIG. 2 of the accompanying drawing recapitulates and shows the results obtained on the 4th day when a man took, twice a day at 12 hour intervals, the same dose of 200 mg of theophylline alone or associated with 100 mg of idrocilamide. The time in hours (t) after the morning dose is plotted on the x-axis, the time 0 corresponding to the dose of medicine on the 4th day. The theophylline blood concentrations in mg/l (th mg/l) are plotted on the y-axis. Curve I corresponds to the results after taking 200 mg of theophylline, curve II corresponds to the results after taking the medicine consisting of 200 mg of theophylline associated with 100 mg of idrocilamide.

Besides an extended blood level being obtained due to the association of idrocilamide with theophylline, it is found that the area under curve II is much greater for the association, even though the same dose of 200 mg of theophylline was administered in both cases.

Since absorption of theophylline orally is very good, this finding indicates that the action mechanism is linked to an interference of idrocilamide on the metabolism of theophylline whose half-life is thus extended. In adults with normal renal functioning, it is known that the dosage of theophylline varies from one patient to the other, despite the good absorption of the medicine. This variation comes from differences in the individuals metabolic capacities. With the idrocilamide acting at the metabolic level, the association permits a better dosage uniformity.

CLINICAL EXAMPLE III

Later, fifteen other asthma patients were treated with the theophylline-idrocilamide association. There were few tolerance problems and the therapeutic results were good. In some cases, particularly favorable results were obtained, with corticoids being cut off.

The foregoing description of the specific embodiments will so reveal the general nature of the invention that others can by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the prasiology or terminology employed herein is for the purpose of description and not of limitation.

What is claimed is:

1. A long-acting theophylline base medicinal composition, comprising a mixture of theophylline with an amount sufficient to increase the theophylline half-life in the blood of a cinnamamide compound of the formula

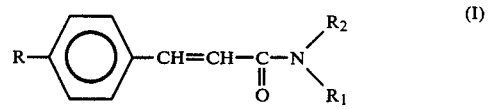

wherein R is hydrogen, halogen or acetyl; $R_1$ is hydrogen or methyl; $R_2$ is

wherein $R_3$ is hydrogen or methyl; or $R_1$ and $R_2$ together with the adjacent nitrogen form 2,2-dimethyl-3-oxazolidinyl.

2. A composition according to claim 1, wherein said cinnamamide is 3-(4-chlorocinnamoyl)-2,2-dimethyloxazolidine.

3. A composition according to claim 1, wherein said cinnamamide is 3-cinnamoyl-2,2-dimethyloxazilidine.

4. A composition according to claim 1, wherein said cinnamamide is idrocilamide.

5. A composition according to claim 4 in unit dosage form comprising 50–1200 mg of said mixture.

6. A composition according to claim 1 in unit dosage form of a tablet, injectable ampoule or suppository.

7. A composition according to claim 1, wherein the molar ratio of said theophylline to said cinnamamide compound is 1:0.1–7.

8. A composition according to claim 1, wherein the weight ratio of said theophylline to said cinnamamide compound is 2:1 to 1:4.

9. A long-acting theophylline based medicinal composition, comprising a mixture of theophylline in free form or aminophylline form, with an amount sufficient to provide a stable and prolonged theophylline blood level of a cinnamamide compound of the formula

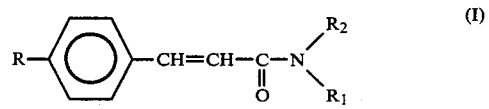

wherein R is hydrogen, halogen or acetyl; $R_1$ is hydrogen or methyl; $R_2$ is

wherein $R_3$ is hydrogen or methyl; or $R_1$ and $R_2$ together with the adjacent nitrogen form 2,2-dimethyl-3-oxazolidinyl.

10. A composition according to claim 9, wherein said theophylline is in the form of aminophylline.

11. A method of treating asthma comprising administering to a patient in need of said therapy, a therapeutic amount of the composition of claim 1.

12. A method according to claim 11, wherein said therapeutic amount comprises 50–1200 mg of said mixture.

13. A method according to claim 7, wherein said composition is administered twice per day at approximately 12 hour intervals.

* * * * *